United States Patent [19]

Cohen

[11] 4,203,452

[45] May 20, 1980

[54] EFFICIENCY OF HUMAN LEARNING EMPLOYING THE ELECTROENCEPHALOGRAPH AND A LONG-TERM LEARNING DIAGNOSTIC-REMEDIAL PROCESS

[76] Inventor: David B. Cohen, 704 W. McMinn Ave., Dade City, Fla. 33525

[21] Appl. No.: 823,431

[22] Filed: Aug. 10, 1977

[51] Int. Cl.$^2$ ............................................... A61B 5/04
[52] U.S. Cl. .................................................. 128/732
[58] Field of Search ......... 128/2.1 M, 2.1 B, 731–732; 35/8 R

[56] References Cited

U.S. PATENT DOCUMENTS

| | | | |
|---|---|---|---|
| 3,548,812 | 12/1971 | Paine et al. | 128/2.1 B |
| 3,877,466 | 4/1975 | Montor | 128/2.1 B |
| 3,880,144 | 4/1975 | Coursin et al. | 128/2.1 B |
| 3,882,850 | 5/1975 | Bailin et al. | 128/2.1 B |
| 3,893,450 | 7/1975 | Ertl | 128/2.1 B |
| 3,896,790 | 7/1975 | Dikmen | 128/2.1 B |
| 3,901,215 | 8/1975 | John | 128/2.1 B |
| 4,008,714 | 2/1977 | Silva et al. | 128/2.1 B |
| 4,031,883 | 6/1977 | Fehmi et al. | 128/2.1 B |

OTHER PUBLICATIONS

Mason, S. M. et al., "Simple Online Detector of Auditory Evoked Cortical Potentials", Med. & Biol. Engr. & Comptrs. vol. 15, Nov. 1977 pp. 641–647.
Marsones, H. J. et al., "A Method for Triggering Evoked Potentials by a Certain Component of Background Activity," Med. & Biol. Engr. vol. 81, pp. 415–418.
Ray, C. D. "Medical Engineering in Research Diagnosis & Therapy" in *Medical Engineering*, (p. 438) Yrbk Med. Publ., Chicago 1974.
"Mind–Power Alpha", Radio Electronics, V.47 #7 pp. 36–39, 91 Jul. 1976.

*Primary Examiner*—Robert W. Michell
*Assistant Examiner*—Francis J. Jaworski

[57] ABSTRACT

A diagnostic and remedial process is provided for improving the efficiency of education by determining when a subject is engaged in long-term learning, resulting in long-term memory by sensing, measuring, displaying, monitoring, recording and analyzing transitional evoked potentials reflecting the occurrence of learning and memory resulting from the chemoelectric reactions in the human brain associated with long-term learning, which produce different end products in respect to both chemical and electrical characteristics than reactions associated with short-term learning, and which are associated with the voltage component, only, of the electroencephalograph (EEG) signal generated by a subject during a learning situation during the diagnostic process an individual teacher/subject counseling arrangement utilizing biofeedback may be enacted in order to accomplish the remedial process of permitting the subject to control his autonomic nervous system.

2 Claims, No Drawings

EFFICIENCY OF HUMAN LEARNING EMPLOYING THE ELECTROENCEPHALOGRAPH AND A LONG-TERM LEARNING DIAGNOSTIC-REMEDIAL PROCESS

The present invention relates to a process for improving the efficiency of human learning by utilizing, analyzing and modifying the generated electrical potentials of human brain waves, collected by use of an electroencephalograph, or any other similar instrument. The process includes the analysis of the brain wave electrical potentials by means of a mental set analyzer and modifier, or any other similar electronic device, adapted to provide a simple, reasonable and convenient means for improving the efficiency of human learning by the analysis and, when necessary, the modification of the learner's brain wave electrical characteristics.

The field of this invention is biocybernetics and is concerned with improved man-machine interaction using the electroencephalograph (EEG) as a new channel of communication. The theory that there is a significant difference between the electrical potentials of brain wave patterns associated with the mental set at the time of short-term learning as opposed to the mental set at the time of long-term learning was tested in an unpublished research project conducted by the inventor, and is the basis for this invention. The purpose of the invention is to provide a means of improving the efficiency of the learning process by the analysis and, as necessary, the modification of the learner's brain wave patterns by use of the EEG, the mental set analyzer and modifier and biofeedback techniques. To the knowledge of the inventor, the electrical potentials of brain wave patterns have not been systematically employed to improve the efficiency of the learning process.

Learning in the existing educational setting is an inefficient process, primarily because the instructor and the learner have no real evidence, at any given instant, during the learning process, whether the learner has the mental set which is conducive to learning.

This invention offers a means of improving the efficiency of education by employing a systems approach with the flexibility of being used as a diagnostic device for individual students; as a remedial device for use in what could be called a "Learning Laboratory" that would be similar to the familiar Reading Laboratory; and as a classroom device which would permit the instructor to sample any individual student, at any given instant, during the class, to determine whether the student's mental set is conducive to long-term learning. New developments in electroencephalographic design appear to make it possible to take brain wave pattern readings without attaching electrodes to the individual. Since the invention being described utilizes the output signal of the EEG, the above mentioned development would make the system more adaptable to classroom and Learning Laboratory use, however, it is not a necessity.

The mental set analyzer and modifier consists of a series of three electronic stages and is designed to accept the output signal of any single channel of an EEG. It can be contained in any suitable box type container constructed of either metal, plastic, or wood. The first stage consists of an electronic voltmeter with a scale from zero to one volt, marked in tenths of volts, and consisting of an operational amplifier, suitable capacitors, resistors and other components shown in the circuit diagram included. This stage, while not absolutely necessary, (a portable meter could be used) does make for a complete packaged device, and measures the signal output of the EEG when a standard test signal of one hundred (100) microvolts is applied to the EEG. This procedure is required so that the sensitivity of the EEG can be properly set for use with the analyzer stage of the invention. The second stage is a voltage analyzer, and a visual display of the voltage analysis. This stage consists of a 339 quad comparator (or similar comparator circuit) suitable resistors, light emitting diodes (LED's), batteries and a potentiometer, as shown in the circuit diagram. The third stage is a voltage controlled oscillator with audio output, descriptive of the level of the analyzed EEG output signal voltage, and consists of transistors, a transformer and suitable condensers and resistors. While the audio output can be achieved with either a speaker, headset type phones, or a single ear-plug type phone, the latter is preferred for purposes of economy and privacy. The circuit of this stage is also included in the overall circuit diagram.

When used as a diagnostic device, the invention would be employed by a psychologist, guidance counselor, or teacher to determine student abilities in achieving the mental set associated with long-term learning. To be so used, a portable EEG would be the desirable, but not the necessary, type, as long as it has an output signal socket and a built-in one hundred (100) microvolt test signal. The sensitivity of the EEG should be set at zero, and the mental set analyzer and modifier input jack plugged into the signal output of the EEG. The sensitivity of the EEG should then be gradually increased until the voltage reading on the voltmeter reads 0.7 volts. The equipment is then ready for use. The electrodes should then be attached to the student, one to the right occipital area of the skull, and one to the right ear lobe. For a controlled diagnostic test of a student, nonsense syllables and a memory drum would be the best method for providing contrived short and long-term learning situations. The mental set analyzer and modifier, by means of the visual LED readout (red lights for inappropriate mental set, and a green light for the proper mental set) and audio output on the ear-plug type phone (the higher the sound frequency, the better the mental set), would indicate any changes in brain wave pattern potentials associated with the student's mental set during the different learning situations. Recall tests of the nonsense syllables learned, under the two situations would establish whether short or long-term learning had occurred. In the case of the combination classroom-Learning Laboratory utilization of the invention, a specially wired room would be desirable for a permanent arrangement. The room could be adapted for any reasonable class size. The student's stations and the teacher's desk could be arranged in either a circle or a square within the perimeter of the room leaving adequate space from the walls for walking. Each student station would consist of a student's seat and desk, an observer's seat, a mental set analyzer and modifier, a portable single channel EEG with its own combined stand and storage cabinet. All stations would be facing in toward the center of the room. Each student station would be wired with a one hundred and twenty (120) volt double outlet receptacle and a double wire to carry the output signal of each EEG at each station to a junction box on the instructor's desk. Numbers on the junction box outlets (either a switch arrangement or jacks) would correspond to the student's station number. In this way, the instructor could switch to or plug in her or his mental set analyzer and modifier so that any student in the class could be monitored at any time. Once that it has been determined that a student is having difficulty in acquiring the mental set required for long-term learning, the Learning Laboratory configuration of the system would be employed. In this configuration, each student station would be isolated by the installation of movable panels. This arrangement gives the student an environment of conducive for successful use of the visual and audio biofeedback facilities included in the invention. The availability of an observer's seat in the cubicle formed by the panels permits the instructor or counselor to assist the student in establishing the knowhow to use the equipment to advantage in achieving the mental set required for long-term learning by actually knowing, by experiencing the inner feeling, that exists when such a mental set is achieved.

The advantages of this invention are that a means of improving the efficiency of the learning process many fold is provided by directly measuring brain wave activity to determine mental set and thereby learning potential during the formal or informal educational process. When inefficiencies are discovered, the invention further provides remedial capability to help the student learn how, by biofeedback, to achieve the desired mental set.

Alternate methods of construction include an alternating current source for power, rather than battery power; meter readings instead of the LED visual readout; four separate operational amplifiers, or transistors or integrated circuits instead of the 339 quad comparator; a voltage controlled amplifier using electronic units other than transistors; and, a counter could be added to record the number of times during a preset period of time the student achieved the mental set associated with long-term learning.

The feature believed to be new is the application that this invention makes of the fact that there is a significant difference between the electrical potential of the brain wave patterns associated with the mental set present when no learning, or short-term learning, as opposed to the mental set present when long-term learning occurs. To take advantage of this difference, the EEG and the mental set analyzer and modifier are employed to analyze systematically the electrical potential of brain wave patterns in order to determine when students have the mental set required to achieve long-term learning; and, also to provide a remedial method for assisting students in need to acquire the ability to develop the brain wave patterns with the potentials required for long-term learning, and therefore the mental set associated with such learning. To the knowledge of the inventor, no process of this nature is now being utilised, or has yet been developed.

It should be understood, of course, that the foregoing disclosure relates to only a preferred embodiment of the invention and that it is intended to cover only changes and modifications of the examples of the invention herein chosen for the purpose of the disclosure, which do not constitute departures from the spirit and scope of the invention as set forth in the appended claims.

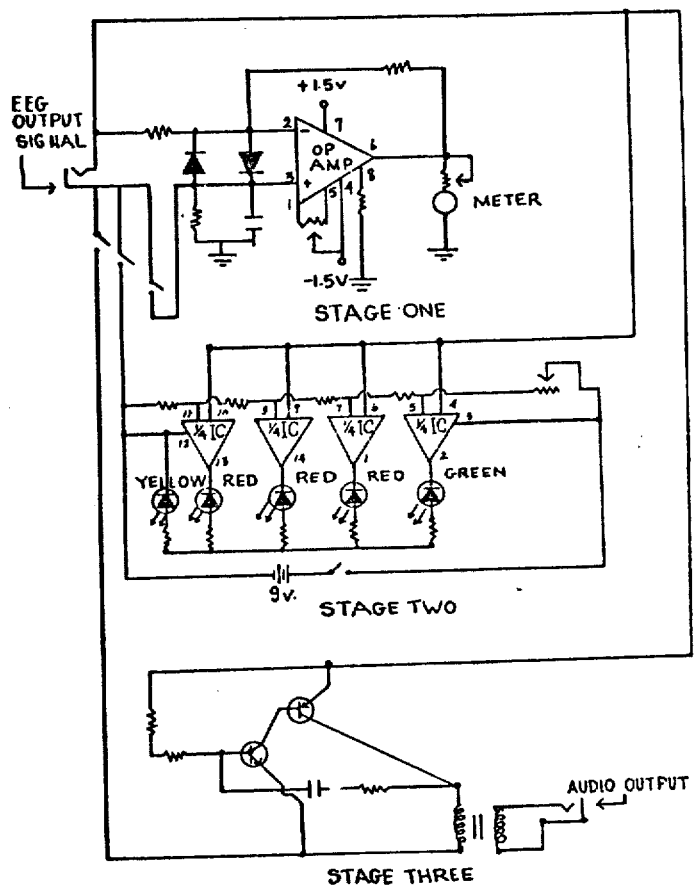

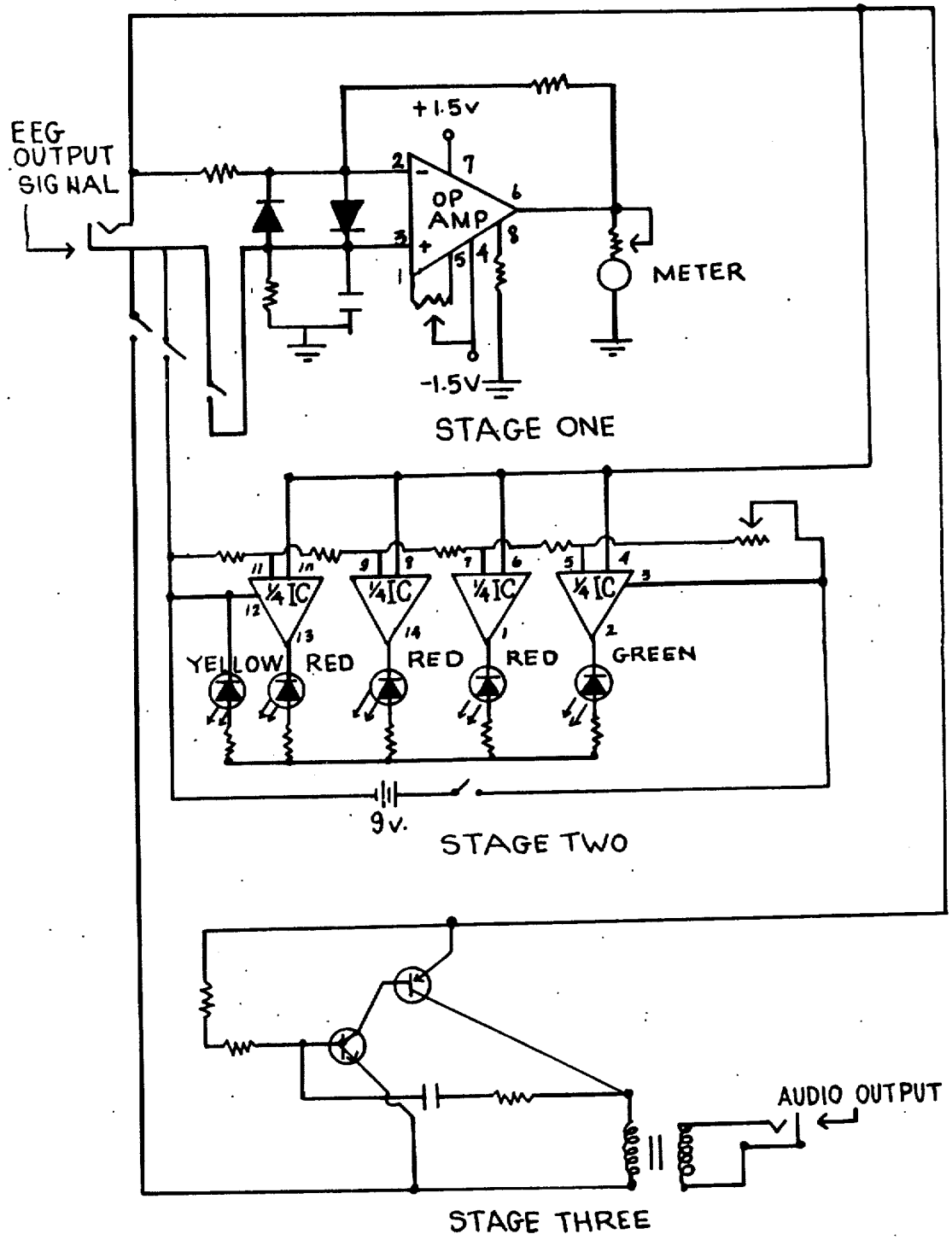

What is claimed is:

1. A method for distinguishing between short-term and long-term learning in a human subject to thereby improve the efficiency of learning in the said human subject, comprising:

pre-determining a threshold value of potential for comparison with the individual's evoked potential representative of the brain wave pattern of a human subject, presenting educational material as a stimulus for learning by the subject, sensing the amplitude of the brain wave potential evoked from the subject by said learning stimulus, comparing the sensed brain wave amplitude with the said pre-determined threshold potential, activating an indicator when the said evoked potential value exceeds the pre-determined threshold potential as an indication of the duration in which long-term learning is occurring.

2. The method of claim 1 further comprising the step of providing the indicator to the said human subject to provide biofeedback control.

* * * * *

UNITED STATES PATENT AND TRADEMARK OFFICE
CERTIFICATE OF CORRECTION

PATENT NO. : 4,203,452
DATED : May 20, 1980
INVENTOR(S) : David B. Cohen

It is certified that error appears in the above—identified patent and that said Letters Patent is hereby corrected as shown below:

The title page should be deleted to insert the attached title page therefor.

The attached sheet of drawing should be insert as the sole sheet of drawing for the above-identified patent.

Signed and Sealed this

Fifth Day of August 1980

[SEAL]

Attest:

SIDNEY A. DIAMOND

Attesting Officer

Commissioner of Patents and Trademarks

United States Patent [19]

Cohen

[11] 4,203,452

[45] May 20, 1980

[54] EFFICIENCY OF HUMAN LEARNING EMPLOYING THE ELECTROENCEPHALOGRAPH AND A LONG-TERM LEARNING DIAGNOSTIC-REMEDIAL PROCESS

[76] Inventor: David B. Cohen, 704 W. McMinn Ave., Dade City, Fla. 33525

[21] Appl. No.: 823,431

[22] Filed: Aug. 10, 1977

[51] Int. Cl.² ............................................. A61B 5/04
[52] U.S. Cl. ............................................. 128/732
[58] Field of Search ......... 128/2.1 M, 2.1 B, 731–732; 35/8 R

[56] References Cited

U.S. PATENT DOCUMENTS

| | | | |
|---|---|---|---|
| 3,548,812 | 12/1971 | Paine et al. | 128/2.1 B |
| 3,877,466 | 4/1975 | Montor | 128/2.1 B |
| 3,880,144 | 4/1975 | Coursin et al. | 128/2.1 B |
| 3,882,850 | 5/1975 | Bailin et al. | 128/2.1 B |
| 3,893,450 | 7/1975 | Ertl | 128/2.1 B |
| 3,896,790 | 7/1975 | Dikmen | 128/2.1 B |
| 3,901,215 | 8/1975 | John | 128/2.1 B |
| 4,008,714 | 2/1977 | Silva et al. | 128/2.1 B |
| 4,031,883 | 6/1977 | Fehmi et al. | 128/2.1 B |

OTHER PUBLICATIONS

Mason, S. M. et al., "Simple Online Detector of Auditory Evoked Cortical Potentials", Med. & Biol. Engr. & Comptrs. vol. 15, Nov. 1977 pp. 641–647.
Marsones, H. J. et al., "A Method for Triggering Evoked Potentials by a Certain Component of Background Activity," Med. & Biol. Engr. vol. 81, pp. 415–418.
Ray, C. D. "Medical Engineering in Research Diagnosis & Therapy" in *Medical Engineering*, (p. 438) Yrbk Med. Publ., Chicago 1974.
"Mind-Power Alpha", Radio Electronics, V.47 #7 pp. 36–39, 91 Jul. 1976.

*Primary Examiner*—Robert W. Michell
*Assistant Examiner*—Francis J. Jaworski

[57] ABSTRACT

A diagnostic and remedial process is provided for improving the efficiency of education by determining when a subject is engaged in long-term learning, resulting in long-term memory by sensing, measuring, displaying, monitoring, recording and analyzing transitional evoked potentials reflecting the occurrence of learning and memory resulting from the chemoelectric reactions in the human brain associated with long-term learning, which produce different end products in respect to both chemical and electrical characteristics than reactions associated with short-term learning, and which are associated with the voltage component, only, of the electroencephalograph (EEG) signal generated by a subject during a learning situation during the diagnostic process an individual teacher/subject counseling arrangement utilizing biofeedback may be enacted in order to accomplish the remedial process of permitting the subject to control his autonomic nervous system.

2 Claims, 1 Drawing Figure